United States Patent [19]

Kirchanski et al.

[11] Patent Number: 4,882,284
[45] Date of Patent: Nov. 21, 1989

[54] METHOD FOR QUANTITATING AND DIFFERENTIATING WHITE BLOOD CELLS

[75] Inventors: Stefan J. Kirchanski, Framingham; Kathleen Wardwell, Roxbury, both of Mass.

[73] Assignee: Ortho Pharmaceutical Corporation, Raritan, N.J.

[21] Appl. No.: 37,769

[22] Filed: Apr. 13, 1987

[51] Int. Cl.[4] ............... G01N 15/10; G01N 21/75; G01N 33/50
[52] U.S. Cl. .................... 436/63; 250/461.2; 356/39; 424/3; 436/172
[58] Field of Search ............... 436/63, 164, 172, 909; 422/73; 250/461.2; 356/39; 424/3

[56] References Cited

U.S. PATENT DOCUMENTS

| 4,325,706 | 4/1982 | Gershman et al. | 356/39 X |
| 4,336,029 | 6/1982 | Natale | 250/461.2 |
| 4,400,370 | 8/1983 | Kass | 424/3 |
| 4,463,099 | 7/1984 | Baroncell et al. | 436/546 |
| 4,485,175 | 11/1984 | Ledis et al. | 436/63 |
| 4,492,752 | 1/1985 | Hoffman et al. | 435/7 |
| 4,513,087 | 4/1985 | Giuliani et al. | 436/111 X |
| 4,596,035 | 6/1986 | Gershman et al. | 356/39 X |
| 4,599,307 | 7/1986 | Saunders et al. | 436/63 X |
| 4,637,986 | 1/1987 | Brown et al. | 436/10 |
| 4,727,020 | 2/1988 | Recktenwald | 436/63 X |

FOREIGN PATENT DOCUMENTS 0121262  10/1984  European Pat. Off. ............. 436/63

Primary Examiner—Robert J. Hill, Jr.
Attorney, Agent, or Firm—Richard J. Grochala

[57] ABSTRACT

A method is provided for discriminating white blood cells from red blood cells and platelets in an unlysed, whole blood sample. The white blood cells may be discriminated into five subpopulations: lymphocytes, monocytes, neutrophils, eosinophils and basophils. A red light absorbing fluorescent dye is utilized along with a measurement system comprised of a red light source and suitable detectors for red fluorescence, forward light scatter and right angle scatter.

24 Claims, 1 Drawing Sheet

METHOD FOR QUANTITATING AND DIFFERENTIATING WHITE BLOOD CELLS

BACKGROUND OF THE INVENTION

Throughout this application, various patents and papers are referenced. The disclosures of these patents and papers in their entireties are hereby incorporated by reference into this application in order to more fully describe the state-of-the-art as known to those skilled therein as of the date of the invention described and claimed herein.

This invention relates to a method for discriminating white blood cells from red blood cells and platelets in unlysed, whole blood by use of a red-fluorescent dye and flow cytometry techniques.

The need to supply the clinical environment with automated instrumentation has forced the development of a wide variety of instruments capable of performing various types of blood cell counts. Automated counting of red blood cells (erythrocytes), platelets and leucocytes (white blood cells) may be accomplished by a variety of techniques. One class of instruments for use in counting blood cells includes those based on flow cytometry principles.

Flow cytometry combines many of the advantages of microscopy and biochemical analysis in a single high precision technique for the rapid analysis and sorting of individual cells. The cells to be measured by this technique are introduced into the center of a fast moving fluid stream and forced to flow single file out of a small diameter orifice at uniform speeds. The particles are hydrodynamically focused to the center of the stream by a surrounding layer of sheath fluid. The cells within the stream pass a measurement station where they are illuminated by a light source and measurements are made at rates of $2.5 \times 10^2$ to $10^6$ cells per minute. Laser light sources are used in the measurement of the cells. Typical laser light sources used include argon ion lasers (UV, blue and green light), krypton lasers (yellow and red light), helium-cadmium lasers (UV and blue light), and helium-neon lasers (red light).

When a cell in the flow stream passes through the light beam, the illuminating light is scattered by the cell and the intensity of scatter at different angles yields information about cell size and surface morphology. Although the light is scattered in all directions, the intensity of light scattered at low angles in the forward direction along the axis of the illuminating laser beam (forward angle light scatter; FALS) is related to the cell size. For example, lymphocytes have little FALS and can be typically distinguished from larger granulocytes with a greater FALS, while monocytes display FALS values which are about the same as granulocytes.

The light scattered by the cells and collected orthogonally to the laser beam (90° right angle or wide-angle light scatter) mostly represents light reflected from the internal or surface structures of the cell and is interpreted as an index of cellular granularity. Use of the combination of FALS and right-angle scatter parameters is more reliable than either parameter alone in discriminating different classes of human blood cells. In addition to these two parameters, fluorochromes may also be used to label the cells of interest. The fluorescence emitted by the cells when excited by the illuminating laser beam yields additional information about the cells for distinguishing subpopulations of cells.

U.S. Pat. No. 3,883,247 (Adams) describes a composition and method for the differential analysis of white blood cells into six categories, namely lymphocytes, monocytes, neutrophils, eosinophils, basophils and immature granulocytes. The white blood cells are treated under conditions in which the cells are "shocked" by exposure to a non-physiological medium, namely a hypotonic aqueous salt solution, during staining with the metachromatic fluorochrome dye acridine orange. The method involves suspending a fresh blood sample in the hypotonic aqueous acridine orange solution for a time period and then subjecting the suspension to radiation from a blue laser. The cells are then differentially classified on the basis of the differences in the magnitudes of red and green fluorescence emitted from individual cells in response to excitation from the blue laser radiation.

A problem with the method taught by Adams is that it requires the use of an argon-ion laser for providing radiation having a wavelength in the blue spectrum for exciting the acridine orange fluorophor. The argon-ion laser is an expensive light source and it would be much more desirable to utilize a light source that provides radiation in the red spectrum, such as the helium-neon laser. An additional problem of the Adams method, is that it only uses the parameter of fluorescence to differentiate the white blood cells. As such, there is no means for distinguishing cells based on cell size, such as the FALS parameter used in flow cytometry techniques. Thus, the Adams method is not suitable for quantitating and differentiating red blood cells, platelets and the sub-populations of white blood cells all in one procedure.

Further problems exist with the method taught by Adams. The use of the hypotonic diluent causes the size of the red blood cells to change. This is a disadvantage when an accurate size measurement of the cells is needed to provide an accurate quantitation of the cells. Also, the red cells absorb the acridine orange thereby changing the effective concentration of the dye in the sample. This results in less dye available to stain the white cells. This problem is difficult to alleviate because of the narrow range of effectiveness of the acridine orange. Use of too high a concentration of the dye results in all the cells absorbing a maximum amount of dye thereby preventing differentiation of the cells. Use of too low a concentration of the dye results in no staining at all.

It is an object of the present invention to provide a method for discriminating white blood cells from red blood cells and platelets as well as quantitating the red blood cells, platelets and white blood cells. A white blood cells differential of at least four-parts is obtained in a single procedure using flow cytometry techniques. It is an additional object of the present invention to achieve the differential of the white blood cells by use of a red fluorescent dye, such as an oxazine dye, having a wide effective range of concentration which is capable of being excited by an inexpensive light source such as a helium-neon laser.

The assignee hereof presently commercially offers the ELT series of instruments which are capable of providing red blood cell, white blood cell and platelet counts. Additionally, the following five traditional parameters are also provided: HGB (hemoglobin), HCT (hematocrit), MCV (mean cell volume), MCH (mean cell hemoglobin) and MCHC (mean cell hemoglobin concentration). The ELT series provides a three-part differential white blood cell count, namely lymphocytes, granulocytes and monocytes. There has been demand for an instrument which can provide a four-part or a five-part differential of white blood cells by further differentiating the granulocytes into neutrophils, basophils and eosinophils.

The prior methods which achieved a three-part differential of white blood cells required a two-step dilution of the patient blood sample in which the red blood cells were lysed. Lysis was required because the prior methods could not distinguish white blood cells from red blood cells. The red blood cells were lysed in order to remove them from the sample and prevent interference with white blood cell analysis. A major shortcoming of the lysis method is that some red blood cells are lysis resistant. Additionally, the lysing reagent also either lyses white blood cells or deleteriously affects the scatter characteristics of the white blood cells. Such results disadvantageously affect the accuracy of the cell counts.

U.S. Pat. No. 4,284,412 (Hansen et al.) describes an automated method for enumerating subclasses of blood cells in a blood sample. The method involves lysis of the red blood cells in the sample to be analyzed and then counting leucocyte subclasses, namely lymphocytes, monocytes and granulocytes. A flow cytometry system is used to measure right angle scatter, forward angle scatter and green fluorescence values. An FITC label and an argon-ion laser are used to generate the green fluorescence values.

U.S Pat. Nos. 3,916,205 and 4,146,604 (both in the name of Kleinerman) describe a method and composition for the counting of leucocytes, erythrocytes, reticulocytes and the differential counting and classification of leucocytes. A dye composition containing three different types of dyes (ethidium bromide, brilliant sulfaflavine and a stilbene disulfonic acid derivative) is described for distinguishing lymphocytes, monocytes, neutrophils and eosinophils. The method involves preparing an alcohol fixed blood smear on a glass slide. The blood smear is irradiated with three different light sources (UV, violet and green) in order to detect the differential staining of the cells.

Shapiro et al. used the same dye composition developed by Kleinerman in a flow cytophotometer to obtain a five-part differential of white blood cells, namely lymphocytes, monocytes, neutrophils, eosinophils and basophils (Shapiro, H. M. et al., J. Hist. and Cyt. (1976), 24: 396–411; Shapiro, H. M., J. Hist. and Cyt. (1977), 25: 976–989). The method described involves first fixing a blood sample with glutaraldehyde in an isotonic solution while avoiding lysis of the cells in order to enhance dye uptake. The dye composition is added after the cells are fixed and is then further diluted to enable an optimal cell sampling rate to be obtained in the cytophotometer. The parameters of forward angle scatter, right angle scatter and three different levels of fluorescence are measured. Three different lasers are used to irradiate the sample.

U.S Pat. No. 4,376,820 (Giannini et al.) describes a method for the quantitative evaluation of the total number of leucocytes and the number of granulocytes, monocytes and lymphocytes in a blood sample. The method involves forming an adduction of the leucocytes, an oxazine dye and a quencher molecule in a isotonic aqueous solution. The resultant adduct is subjected to radiation by a first ray of pulse light and then with a second ray of monochromatic light. The exit optical intensity of the latter ray of light is analyzed as a function of time. Before treatment of the cells, the blood sample is separated into white cells and red cells or the white cells are first concentrated.

U.S. Pat. No. 4,400,370 (Kass) describes a manual technique for analyzing human blood wherein a 5-part differential of white blood cells is achieved. The method involves contacting a whole blood sample with the dye basic orange #21 to distinguish lymphocytes, neutrophils, eosinophils, basophils and monocytes. This patent describes the use of one unique dye, namely basic orange #21, and no other dyes are exemplified. The patent describes that the dye used must be metachromatic in order to achieve the differentiation of the cells. It is suggested that the class of oxazines have a few species which would be operative in the method described. The method described requires manual microscopic analysis of cell morphology and therefore, does not work in a flow cytometry system.

U.S. Pat. No. 4,463,099 (Baroncelli et al.) describes the use of oxazines as immunofluorescent reagents. The immunofluorescent reagent described is prepared by reacting a protein to be labelled, a cross-linking agent and an oxazine dye.

SUMMARY OF THE INVENTION

The present invention provides a method for discriminating white blood cells from red blood cells and platelets in unlysed, whole blood. The method comprises providing an aliquot from the blood to be studied and then diluting the aliquot in one step with an isotonic solution containing a red light absorbing, fluorescent dye. The dye is excited by long wavelengths of radiation, i.e., the red spectrum, and also emits radiation in the red spectrum. Lysis of the blood cells is not required in the present method. The blood cells are permitted to be in contact with the dye for a suitable time period thereby differentially staining the cells. At least a portion of the diluted aliquot, substantially a cell at a time, is passed through an area of red fluorescent optical stimulation. The area may have a cross-sectional dimension which is only somewhat larger than the expected dimension of the cells. As the cells pass through this area, forward angle light scatter, right angle light scatter and red fluorescence from the stimulated cells are detected and measured. The white blood cells are then discriminated from the red blood cells and platelets on the basis that the white blood cells have different forward angle scatter, right angle scatter and red fluorescent staining properties than the red blood cells and platelets.

The method of the present invention discriminates white blood cells into at least four subpopulations, namely lymphocytes, monocytes, neutrophils and eosinophils. Additionally, a fifth subpopulation, basophils, may also be differentiated.

The present invention also provides a dye composition for the quantitation of white blood cells and the differentiation of the white blood cells into at least four subpopulations by fluorescence using flow cytometry. The composition comprises an isotonic solution containing a red light absorbing, fluorescent dye capable of differentially staining the subpopulations of white blood cells wherein the dye does not lyse blood cells. In a preferred embodiment the dye is an oxazine dye. A preferred oxazine dye is oxazine 170.

Existing cell counters for use in clinical hematology employ some type of red blood cell lysis to detect relatively few white blood cells among many red blood cells. The reason for this is that prior techniques cannot sufficiently distinguish white blood cells from red blood cells in a sample unless the red blood cells are first removed. A major shortcoming of the lysis method is its sensitivity to lysis resistant red blood cells. The present invention provides a method for overcoming this drawback through the use of a red light absorbing, fluorescent dye composition which does not lyse blood cells.

The dye of the present invention is dissolved in an isotonic solution and used as a whole blood diluent in a one-step dilution. Due to the structural differences between blood cell types, white blood cells develop substantially greater fluorescence when mixed with the present composition than do red blood cells or platelets. Through the use of a suitable red fluorescence excitation and detection system, white blood cells can then be discriminated from red blood cells and platelets in unlysed, whole blood. The red blood cells and platelets exhibit such a low fluorescence that they are easily separated from the white blood cells by an appropriate red fluorescence threshold. Because all cell types remain intact (i.e. no lysis) in this method, counting of leucocytes, erythrocytes and platelets can occur in one dilution.

An advantage to using a red light absorbing fluorescent dye is that it permits the use of a red laser, such as a helium-neon laser, as the excitation source. Helium-neon lasers are less expensive than other lasers, such as the argon ion laser, and use thereof reduces the cost of the hematology instrument which incorporates the laser. Furthermore, use of a fluorophore which is excited by and emits in long wavelengths is desirable because the wavelengths can be more easily detectable to the exclusion of natural fluorescence from other biomolecules. Such natural fluorescence otherwise creates a background signal often masking the desired signal from the fluorescent label, thereby lowering sensitivity.

An additional benefit of the present method is that it allows for the discrimination of leucocyte subpopulations. Differences in membrane properties, size and internal structure give rise to differential fluorescent staining properties of the white blood cell subpopulations. Thus, some white cell types will be stained to a greater extent than others, thereby providing these cells with a higher level of fluorescence. In conjunction with forward angle light scatter properties and right angle light scatter properties, this fluorescent phenomenon allows for the enumeration of lymphocytes, monocytes, neutrophils, eosinophils and basophils.

DETAILED DESCRIPTION OF THE INVENTION

Figure 1:
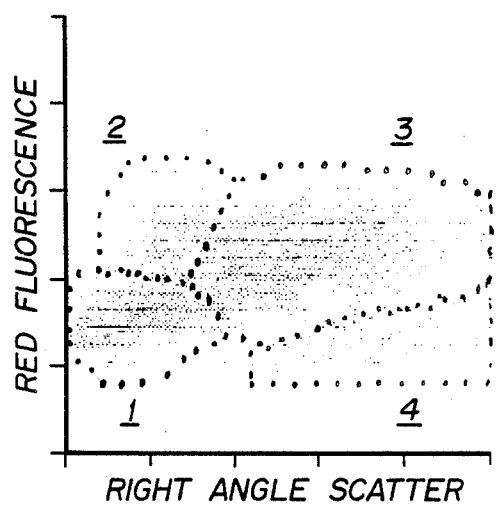
FIG. 1 depicts a white cell cytogram of red fluorescence (ordinate) vs. right angle scatter (abscissa). Each "dot" in the cytogram represents values obtained from one or more leucocytes in the sample analyzed. These cells exhibit a level of red fluorescence which exceeds an electronically set threshold level. Below this threshold, and thus not displayed in the cytogram, are the values obtained from erythrocytes and platelets. Region 1 defines the area in which values for normal lymphocytes are found. Values for monocytes are found in Region 2; for neutrophils in Region 3 and for eosinophils in Region 4.

The present invention provides a method for discriminating white blood cells from red blood cells in an unlysed, whole blood sample obtained from a patient. The method utilizes a red light absorbing, fluorescent dye which may conveniently be stimulated by a red laser, such as a helium-neon laser. The method permits the differentiation of at least four distinct subpopulations of white blood cells. The subpopulations comprise lymphocytes, monocytes, neutrophils and eosinophils. These subpopulations maybe differentiated and enumerated by plotting red fluorescence values versus right angle scatter values in a cytogram. Additionally, a fifth subpopulation of white blood cells may also be differentiated. The fifth subpopulation, basophils, may be differentiated in an alternate cytogram by plotting red fluorescence values versus forward angle scatter values.

The red light absorbing, fluorescent dye of the present invention may be any red light absorbing dye capable of producing adequate enumeration and differentiation of leucocytes. The dye may be capable of penetrating all blood cells, i.e. white blood cells, red blood cells and platelets, but due to the natural differences between blood cell types (i.e. differences in internal cellular structures) substantially greater fluorescence develops in white blood cells. Certain positively charged organic dyes work particularly well for cytochemically staining blood cells. Thus, a suitable dye has the characteristics of being a positively charged organic dye capable of crossing the blood cell membrane and cytochemically staining the blood cells, i.e. staining cellular granules or binding to cytoplasmic components.

For all intents and purposes, the red blood cells can be regarded as non-fluorescent because it is believed that they take up less dye than other cells and they are separated from the white cells by an appropriate fluorescence threshold. Additionally, differences between the subpopulations of white blood cells in terms of membrane properties, nuclear structure, size and internal cellular granularity give rise to differential right angle light scatter and fluorescent staining properties. These differences in properties allow both the enumeration of leucocytes and the discrimination between white blood cell subtypes in a relatively unaltered whole blood milieu.

A suitable class of red absorbing fluorescent dyes is the class of oxazine dyes. The oxazine dyes utilized are positively charged and capable of crossing blood cell membranes and staining granules or binding to cytoplasmic components.

Examples of suitable oxazine dyes are those having the structural formulas of I or II below:

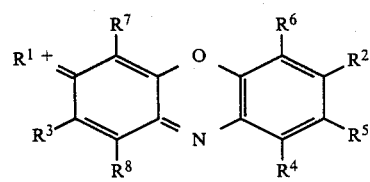

-continued

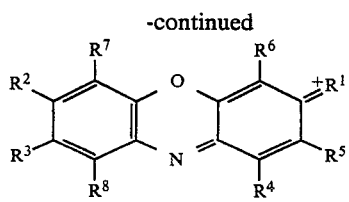

wherein, $R^1$ and $R^2$ are primary, secondary or tertiary amines which may be the same or different and which are capable of forming a resonance structure with the ring nitrogen in the center ring of the structure. Furthermore, the positively charged double bond forms with the nitrogen of $R^1$. The secondary and tertiary amines may be substituted with alkyl, aryl, arylalkyl or alkylaryl radicals. $R^3$, $R^6$, $R^7$ and $R^8$ may be H or $C_1$-$C_4$ alkyl. $R^4$ and $R^5$ taken individually may be H or $C_1$-$C_4$ alkyl or taken together with the two carbons to which they are attached may form a benzene ring, i.e. so that a naphthalene ring structure results.

Suitable alkyl and aromatic substituents for $R^1$ and $R^2$ are as follows:

$NH_2$, NH(methyl), N(methyl)$_2$, NH(ethyl), N(ethyl)$_2$,

NH(n-propyl), N(n-propyl)$_2$, NH(n-butyl), N(n-butyl)$_2$,

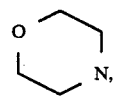

NH(benzyl), NHCH$_2$CH$_2$NHCH$_2$COOH,

NHCH$_2$CH$_2$NH—C(=O)—(phenyl), NHCH$_2$COOH, NH(CH$_2$)$_2$NH$_2$

-continued or 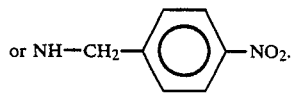

The cationic oxazine dyes may be prepared as salts of a suitable anion such as Cl$^-$, ClO$_4^-$, NO$_3^-$ or $CH_3CO_2^-$. Preferably, the anion is Cl$^-$, which has been shown to form a more stable dye composition.

A preferred group of oxazine dyes are those having structure I, wherein:

$R^1$ is N(ethyl)$_2$, NH(ethyl), N(n-butyl)$_2$ or

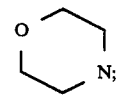

$R^2$ is NH(benzyl), NHCH$_2$CH$_2$NHCH$_2$COOH,

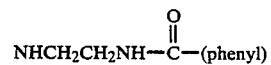

or NH(C$_2$H$_5$); and
$R^3$ is H or methyl.

A preferred oxazine is oxazine 170, which has the structure:

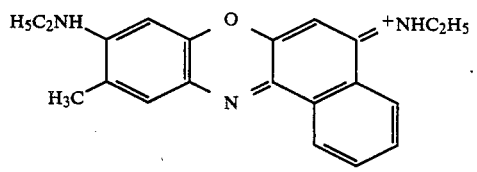

Additional oxazines which provided a good differential of white blood cells have the following structures:

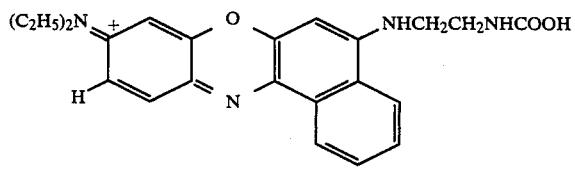

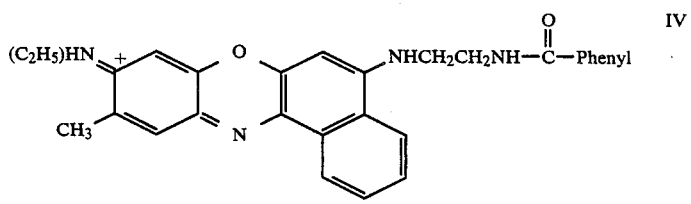

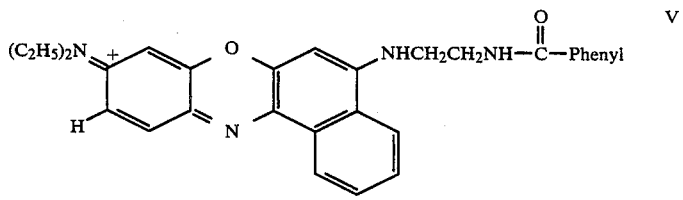

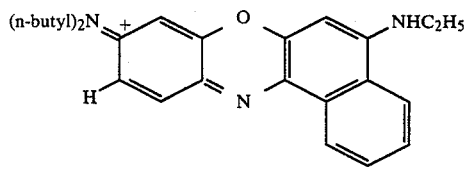

VI

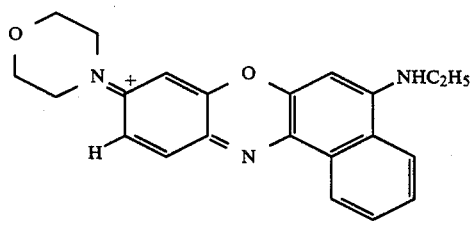

VII

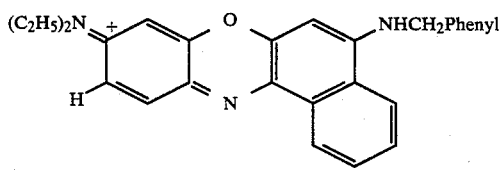

VIII

The oxazine dyes of the present invention have a maximum excitation wavelength in the spectral range of about 610 nm to about 660 nm and more optimally 610–635 nm. The maximum emission wavelength range for the dyes is in the range of about 620 nm to about 710 nm and more optimally 640–690 nm. Any light source capable of providing an excitation wavelength in the range of 610–660 nm may be used as a source of red optical stimulation for the oxazine dyes. The helium-neon laser is such a light source, having an emission wavelength of about 632.8 nm.

Oxazine 170 (also referred to in the literature as oxazine 720) is a laser-pumpable, efficient laser dye and has a maximum absorption wavelength of about 623 nm. As such, this molecule is efficiently excited by the helium-neon laser. In a preferred embodiment, the chloride salt of oxazine 170 is utilized in the present method. The chloride anion dissociates from the dye cation in solution, permitting optimum fluorescent efficiency.

The chromophore of the dye of the present invention consists of the ring nitrogen atom and the nitrogen atoms of the amino groups of $R^1$ and $R^2$. The positive charge on the molecule can resonate back and forth between $R^1$ and $R^2$, wherein the nitrogen possessing the positive charge also has a carbon-nitrogen double bond. Other functional groups known to those skilled in the art which can stabilize a reasonance structure may be substituted for the amino groups at $R^1$ and $R^2$. One such functional group is the phenolic hydroxyl group.

In the method of the present invention, the red light absorbing fluorescent dye is contained in a physiological medium, such as an isotonic solution having an approximately neutral pH. The isotonic solution may be a saline solution. Maintaining the tonicity of the solution through a proper balance of anions and cations is important for achieving the appropriate staining reaction. This isotonic solution is used as the diluent of the blood sample aliquot in a one-step dilution. Optimization of the dye concentration, the ionic balance and the amount of time the cells are exposed to the dye reagent permits the differentiation of the white blood cells into lymphocytes, monocytes, neutrophils, eosinophils and basophils.

The concentration of the dye in the present composition is suitably within the range of about 0.001 mM to about 3.0 mM and preferably within the range of 0.01–0.03 mM. A preferred dye concentration is 0.02 mM. A suitable time for the blood cells to be in contact or mixed with the dye is from about 5 to about 90 seconds.

The dye composition of the present invention is preferably buffered in the pH range 7.1–7.9. Buffering may be accomplished by a phosphate buffer system, however, any other buffer capable of maintaining the appropriate pH is also quite suitable. Other suitable buffers are HEPES and DIPSO (organic nitrogen containing buffers of the "Good" series).

The present dye composition may also contain a bacteriologic preservative such as 1,3 dimethylol-5,5-dimethylhydantoin. This component may be replaced by one of many other compounds with bacteriostatic or bacteriocidal properties. Diazolidinyl urea or chloroacetamide present two possibilities. A suitable amount of preservative is within the range of about 0.05%–0.4% (v/v) of the aqueous dye composition. For further stabilization of the reagent, a small amount of EDTA may be added. The EDTA is not critical to reagent performance and it may be omitted without adverse effects.

The dye composition may also contain an osmotic balancing compound or tonicity agent to preserve the integrity and shape of the cells being measured. Sodium chloride is an important constituent of blood serum and use thereof is a convenient solution to the problem of maintaining a proper osmotic balance (e.g., that present in normal whole blood). Other osmotic balancers such as mannitol or sorbitol represent reasonable alternatives. The amount of tonicity agent in the composition should be sufficient to maintain the osmolarity within the range of about 250 mosm to about 330 mosm (isotonicity is about 280–295 mosm).

A surfactant may also be added to the dye composition to improve the fluidic properties of the reagents in the mechanical system. Triton X-705 (polyethylene glycol octylphenol ether) is a suitable surfactant. Other surfactants which are not harmful to the cells, such as the Pluronics, represent alternatives. A suitable amount of surfactant is within the range of about 0.04% to about 0.06% (v/v).

The present invention utilizes a measurement system comprised of a red light source and suitable detectors for red fluorescence, forward light scatter and right angle scatter. As the blood cells pass through the area of optical stimulation in the flow cytometer, photosensors within the instrument measure the light characteristics of each cell, namely forward angle scatter, right angle scatter and red fluorescence. The photosensors generate electrical signals which are amplified for subsequent analysis. The output of the data collected by the instrument may be a plot of the amplitudes of the signals generated in a cytogram. Preferably, a computer program is utilized to plot and analyze the data. Two useful cytograms are the plot of red fluorescence values vs. right angle scatter values and the plot of red fluorescence values vs. forward angle scatter values.

As used herein the term "cytogram" means a representation of cell data as a plot of dots, wherein each dot on the cytogram represents many cells. A 16 level gray scale is used to represent each dot, wherein the brightness or size of the dot displayed on a cathode ray tube (CRT) indicates the number of cells present. The location of the dot is given by coordinates which are proportional to selected parameters characteristic of each cell type. Clusters or aggregates of dots on the cytogram represent groups of cells of similar type.

Computer programs may be written to automatically acquire the cell data in cytogram form (also known as a two-dimensional histogram). This is a two dimensional array of points representing two parameters of interest. The resolution of the parameters which make up the array must be sufficient to adequately represent and differentiate the various clusters. A method for enumerating three-part white blood cell differential clusters is described in U.S. Pat. No. 4,596,035 (Gershman et al.).

Flagging of abnormal samples can occur whenever cluster counts, shapes or location exceed preset limits or whenever two clusters interfere with each other by being "overlapping" and thus possibly creating incorrect cluster counts. The operator is notified of such flagging conditions either by audible signals or indications on the result format (i.e., CRT screen, hardcopy).

In terms of forward angle scatter values, the following relationship exists among blood cell types:

---
platelets < red blood cells < = lymphocytes < = basophils < = monocytes < neutrophils and eosinophils

---

Within the granulocyte group, the basophils have the lowest values. The neutrophils and eosinophils have about the same values as each other and they have higher values than the basophils.

With regard to right angle scatter values, the following relationship generally exists among leucocyte subpopulations, however there may be some overlap of groups:

---
< monocytyes and basophils < neutrophils and eosinophils

---

The neutrophils and eosinophils have about the same values as each other. The basophils have approximately the same values as the monocytes.

Red fluorescence values for the various cell types depend on how much dye is taken up by each cell. Red blood cells are believed to take up less dye than the other cells and they may be considered non-fluorescent. Platelets are stained by the dye at about the same level as the granulocytes. However, because each individual platelet is so much smaller than a granulocyte it does not take up as many dye molecules per cell as a granulocyte and, therefore, has a lower fluorescence per cell. Also, the platelets have much lower forward angle scatter values than granulocytes and therefore can be distinguished by size.

The leucocyte subpopulations have the following relationship for red fluorescence values:

---
lymphocytes and eosinophils < monocytes, neutrophils and basophils.

---

Lymphocytes have lower red fluorescence values than monocytes, neutrophils and basophils. The lymphocytes have about the same red fluorescence values as eosinophils. Monocytes, neutrophils and basophils have approximately equivalent values and eosinophils have values less than each of them. Because basophils have lower forward angle scatter values than the other granulocytes, they can be distinguished. The monocytes can be distinguished from the granulocytes on the basis of right angle scatter values. Thus, right angle scatter values and red fluorescence values can be used to distinguish monocytes and granulocytes from lymphocytes as well as distinguishing eosinophils from the other granulocytes.

An advantage of the method of the present invention is that it permits the differentiation of basophils from other subpopulations of white blood cells. Human basophils are the least abundant of the circulating leucocytes. Typically, basophils constitute only about 0.6% of all the circulating white blood cells in a normal, healthy adult. In 95% of healthy adults, basophils never exceed 1.8% of the white blood cell count. The existence of a rapid, reliable method for screening basophils would benefit clinicians because manual methods for counting basophils are slow and imprecise.

Although the low numbers of circulating basophils hampers biomedical research into the role that basophils play in human diseases, basophils do participate in disease processes. For example, elevated levels of basophils have been reported in allergic reactions like bronchial asthma, in leukemias of the myeloproliferative type like CML (chronic myelogenic leukemia), and in ulcerative colitis. Thus, knowing the numbers of basophils in whole blood will enable a clinician to detect or monitor the progress of these and perhaps other diseases.

The invention will be further clarified by a consideration of the following example, which is intended to be purely exemplary of the use of the invention.

EXAMPLE 1

The present methods may be carried out in an "InCyte" hematology analyzer (Ortho Diagnostic Systems, Inc.). This instrument uses the detection of red fluorescence to differentiate leucocytes from erythrocytes and platelets. Further, by controlling the concentration of the dye, its diluent constituents and staining time, and by making additional light scatter measurements, this instrument is capable of discriminating subtypes of leucocytes.

The dye composition employed was made up by mixing the following ingredients in one liter of distilled water:

| Compound | Preferred Amount | Operative Range |
|---|---|---|
| Oxazine 170 (chloride salt) | 7 mg | 5 mg–10 mg |
| 1,3 Dimethylol-5,5-Dimethylhydantoin | 1.82 ml | 0.91 ml–3.64 ml |
| Sodium Chloride | 7.5 g | 7 g–8 g |
| Potassium Phosphate (monobasic) | 0.124 g | 0.112 g–0.136 g |
| Potassium Phosphate (dibasic) | 2.12 g | 2 g–2.4 g |
| Triton X-705 | 0.5 ml | 0.4 ml–.6 ml |
| EDTA (disodium, dihydrate) | 0.2 g | 0 g–0.4 g |
| Distilled water | sufficient to make one liter | |

The ranges of pH and osmolarity may be somewhat broader than allowed for in the above composition. In effect, the composition will perform adequately at pH 7.1–7.9 and with osmolarity from 250 mosm. to 330 mosm. The "InCyte" instrument measures erythrocyte volume in this reagent. Therefore, this restricts the reagent to having near isotonicity in order to prevent volume changes of the erythrocytes.

While the dye constituent is obviously the active ingredient, the other components play an important role in the development of staining the blood cells by maintaining the integrity of the leucocytes and, in some cases, influencing dye uptake by the cells.

The dye composition described above was used by "InCyte" to dilute whole blood and stain the blood cells therein. Whole blood was aspirated by the instrument and approximately 40 microliters was diluted with approximately 1600 microliters of the above described dye composition (1:40 dilution ratio). The solution was drawn into a chamber and mixed for about eight seconds. The dye/blood mixture was then pumped into a flow cell where blood cells were passed single file through a red laser beam (helium-neon). In this manner, light scatter and fluorescence measurements were made on individual cells. The measurements were made during the time window in which maximum fluorescence was developed for the conditions and composition described (e.g., 23–40 seconds). This permitted easy discrimination of leucocytes from erythrocytes and platelets. The erythrocytes and platelets were counted by forward light scatter. Next, the sample flow was increased so that multiple cells passed through the laser beam simultaneously. During this phase, red fluorescence was used to discriminate the brightly fluorescent leucocytes from the dimly fluorescent erythrocytes (several of which were present with each leucocyte as it passed through the laser beam).

Figure 2:
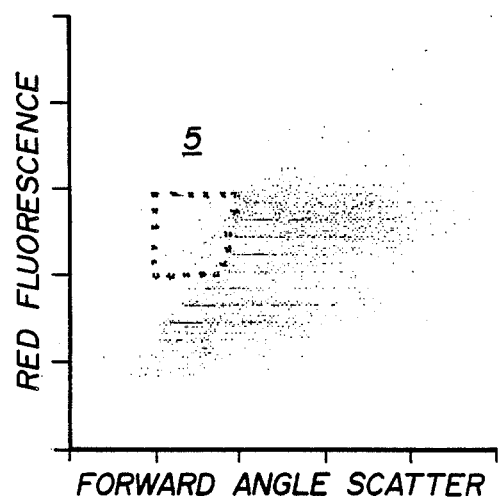
FIG. 2 depicts a white cell cytogram of red fluorescence vs. forward angle scatter. This cytogram represents the same sample as in FIG. 1, except that forward angle light scatter has been substituted for right angle scatter. In this representation, basophils may be enumerated by counting cells which fall in Region 5.

Because leucocyte subtypes have different membrane and internal structural properties, the cells' dye uptake and inherent light scatter characteristics vary enough to provide differentiation of five categories, as depicted in FIGS. 1 and 2. Lymphocytes and eosinophils develop less fluorescence than do monocytes and neutrophils, and therefore are represented by regions 1 and 4 respectively of FIG. 1. Neutrophils and eosinophils exhibit greater right angle scatter than do lymphocytes and monocytes, and therefore are represented by regions 3 and 4 respectively of FIG. 1. When these two parameters are plotted against each other, clusters representing these cell types arise in four quadrants and may be enumerated. The erythrocytes that were present in the laser beam with each leucocyte had very little right angle scatter and contributed only a slight smearing (in the horizontal direction) of the clusters. The cluster representing the fifth subtype, basophils (represented by region 5), became apparent when plotting forward angle scatter vs. red fluorescence. In this case, the basophils showed low forward angle scatter and high red fluorescence while the other subtypes exhibited either low forward angle scatter, low red fluorescence or high forward angle scatter, high red fluorescence. It must be kept in mind that the erythrocytes were largely removed from consideration by using the red fluorescence to electronically threshold the results.

It is apparent that the five subtypes of leucocytes are readily identified by the present method. These five subtypes represent what can be expected in normal blood samples. For abnormal blood samples containing other cell types, additional clusters may appear in other than the previously described positions or may overshadow existing clusters to an extent which does not allow accurate differentiation of subtypes. A "flag" condition arises in these situations, whereby the sample is identified as containing abnormal cell types.

A display of a normal blood result in which red fluorescence is plotted against right angle scatter is shown in FIG. 1. A plot of red fluorescence vs. forward angle scatter for the same sample is shown in FIG. 2.

Other embodiments of the invention will be apparent to one skilled in the art from a consideration of this specification or practice of the invention disclosed herein. It is intended that the specification and examples be considered as exemplary only, with the true scope and spirit of the invention being indicated by the following claims.

What is claimed is:

1. A method for discriminating white blood cells from red blood cells and platelets in unlysed, whole blood comprising:
   a. providing an aliquot of unlysed, whole blood to be studied;
   b. diluting the aliquot in one step with a reagent consisting essentially of an isotonic solution of a red light absorbing, fluorescent dye, and permitting the aliquot to be in contact with the reagent for a time period sufficient for the dye to differentially stain cells in the aliquot;
   c. passing at least a portion of the diluted aliquot, substantially a cell at a time, through an area and stimulating each cell passed through said area with red fluorescent optical stimulation;
   d. detecting and measuring forward angle light scatter, right angle light scatter and red fluorescence from each stimulated cell; and
   e. discriminating white blood cells from red blood cells and platelets in the aliquot on the basis that white blood cells have different forward angle scatter, right angle scatter and red fluorescent staning properties than red blood cells and platelets.

2. The method of claim 1, wherein the dye is a positively charged organic dye capable of crossing blood cell membranes and cytochemically staining blood cells.

3. The method of claim 2, wherein the dye is such that it causes white blood cells to fluoresce to a greater extent than other blood cells.

4. The method of claim 2, wherein the dye is oxazine 170.

5. The method of claim 1, wherein the dye is an oxazine dye.

6. The method of claim 5, wherein the oxazine dye has the structural formula of I or II:

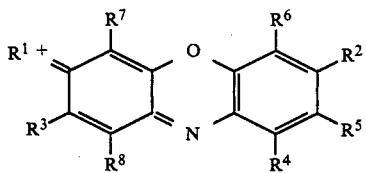

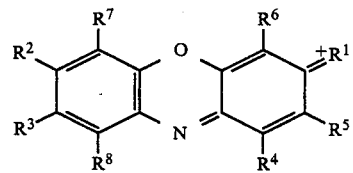

wherein $R^1$ and $R^2$ are primary, secondary or tertiary amines, which may be the same or different, and wherein the positively charged double bond forms with the nitrogen of $R^1$; $R^3$, $R^6$, $R^7$ and $R^8$ are H or $C_1$-$C_4$ alkyl; and $R^4$ and $R^5$ taken individually are H or $C_1$-$C_4$ alkyl or taken together with the two carbon atoms to which they are attached form a benzene ring.

7. The method of claim 6, wherein $R^1$ and $R^2$ are $NH_2$, NH(methyl), N(methyl)$_2$, NH(ethyl), N(ethyl)$_2$, NH(n-propyl), N(n-propyl)$_2$, NH(n-butyl), N(n-butyl)$_2$,

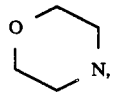

NH(benzyl), NHCH$_2$CH$_2$NHCH$_2$COOH,

NHCH$_2$CH$_2$NH—$\overset{O}{\overset{\|}{C}}$—(phenyl), NHCH$_2$COOH, NH(CH$_2$)$_2$NH$_2$ or 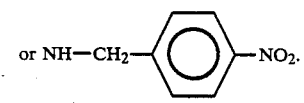

8. The method of claim 7, wherein the dye has the structural formula of I and $R^1$ is N(ethyl)$_2$, NH(ethyl), N(n-butyl)$_2$ or

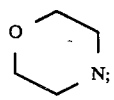

$R^2$ is NH(benzyl), NHCH$_2$CH$_2$NHCH$_2$COOH,

NHCH$_2$CH$_2$NH—$\overset{O}{\overset{\|}{C}}$—(phenyl) or NH(ethyl);

$R^3$ is H or methyl; and $R^4$ and $R^5$ taken together with the carbon atoms to which they are attached form a benzene ring.

9. The method of claim 7, wherein the dye is the salt of an anion.

10. The method of claim 9, wherein the anion is $Cl^{31}$, $ClO_4^-$, $NO_3^-$ or $CH_3CO_2^-$.

11. The method of claim 1, wherein the dye is such that it does not lyse blood cells.

12. The method of claim 1, wherein the red fluorescent optical stimulation is provided by a helium-neon laser.

13. The method of claim 1, wherein white blood cells in the aliquot are differentiated into at least four subpopulations.

14. The method of claim 13, wherein the subpopulations comprise lymphocytes, monocytes, neutrophils and eosinophils.

15. The method of claim 14, wherein the subpopulations are differentiated by plotting red fluorescence values versus right angle scatter values.

16. The method of claim 14, wherein the subpopulations additionally comprise basophils.

17. The method of claim 16, wherein the basophils are differentiated from other blood cells by plotting red fluorescence values versus forward angle scatter values.

18. The method of claim 1, wherein the isotonic solution has a pH within the range of about 7.1-7.9.

19. The method of claim 1, wherein the isotonic solution additionally contains a preservative to prevent bacterial growth.

20. The method of claim 19, wherein the preservative is 1,3 dimethylol-5,5-dimethylhydantoin.

21. The method of claim 1, wherein the time period in step (b) is from about 5 seconds to about 90 seconds.

22. A method for differentiating white blood cells in unlysed, whole blood into at least four subpopulations, comprising:
   a. providing an aliquot of unlysed, whole blood to be studied;
   b. diluting the aliquot in one step with a reagent consisting essentially of an isotonic solution of a red light absorbing, fluorescent dye, and permitting the aliquot to be in contact with the reagent for a time period sufficient for the dye to differentially stain cells in the aliquot;
   c. passing at least a portion of the diluted aliquot, substantially a cell at a time, through an area and stimulating each cell passed through said area with red fluorescent optical stimulation;
   d. detecting and measuring forward angle light scatter, right angle light scatter and red fluorescence from each stimulated cell; and
   e. differentiating at least four subpopulations of white blood cells in the aliquot by plotting red fluorescence values versus right angle scatter values.

23. The method of claim 22, wherein the subpopulations comprise lymphocytes, monocytes, neutrophils and eosinophils.

24. The method of claim 23, where in the subpopulations additionally comprise basophils and wherein basophils are differentiated from other white blood cells by plotting red fluorescence values versus forward angle scatter values.

* * * * *